(12) United States Patent
Watanabe et al.

(10) Patent No.: US 10,391,755 B2
(45) Date of Patent: Aug. 27, 2019

(54) SOLID FREEFORM FABRICATION MATERIAL SET, METHOD OF FABRICATING SOLID FREEFORM OBJECT, METHOD OF FABRICATING DENTAL PROSTHESIS, AND DEVICE FOR FABRICATING SOLID FREEFORM OBJECT

(71) Applicants: Masaki Watanabe, Kanagawa (JP); Tatsuya Niimi, Kanagawa (JP); Teruki Kusahara, Kanagawa (JP); Yoichi Sakurai, Kanagawa (JP); Kohichiroh Tanaka, Kanagawa (JP)

(72) Inventors: Masaki Watanabe, Kanagawa (JP); Tatsuya Niimi, Kanagawa (JP); Teruki Kusahara, Kanagawa (JP); Yoichi Sakurai, Kanagawa (JP); Kohichiroh Tanaka, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 212 days.

(21) Appl. No.: 15/295,232

(22) Filed: Oct. 17, 2016

(65) Prior Publication Data

US 2017/0113411 A1 Apr. 27, 2017

(30) Foreign Application Priority Data

Oct. 23, 2015 (JP) ................................. 2015-209338
Sep. 16, 2016 (JP) ................................. 2016-182144

(51) Int. Cl.
| | | |
|---|---|---|
| B29C 35/04 | (2006.01) | |
| B29C 67/00 | (2017.01) | |
| A61K 6/08 | (2006.01) | |
| A61K 6/083 | (2006.01) | |
| A61C 13/08 | (2006.01) | |

(Continued)

(52) U.S. Cl.
CPC .......... *B33Y 10/00* (2014.12); *A61C 13/0019* (2013.01); *A61C 13/087* (2013.01);
(Continued)

(58) Field of Classification Search
USPC ................. 523/115; 264/240, 241; 427/2.26; 433/218, 222.1, 223
See application file for complete search history.

(56) References Cited

U.S. PATENT DOCUMENTS 6,821,462 B2    11/2004  Schulman
7,381,360 B2 *   6/2008  Oriakhi ..................... B28B 1/00
                                                  264/113

(Continued)

FOREIGN PATENT DOCUMENTS

EP    1 524 098 A1    4/2005
JP    6-218712        8/1994

(Continued)

OTHER PUBLICATIONS

Extended European Search Report dated Mar. 7, 2017 in Patent Application No. 16195156.1.

(Continued)

*Primary Examiner* — Tae H Yoon
(74) *Attorney, Agent, or Firm* — Oblon, McClelland, Maier & Neustadt, L.L.P.

(57) ABSTRACT

A solid freeform fabrication material set includes a material A for solid freeform fabrication and a material B for solid freedom fabrication. The material A includes a polymerization initiator A and at least one of an organic particle and an inorganic particle. The material B includes a polymerizable compound B.

17 Claims, 2 Drawing Sheets

(51) Int. Cl.
  *B33Y 10/00* (2015.01)
  *B33Y 30/00* (2015.01)
  *B33Y 70/00* (2015.01)
  *A61C 13/00* (2006.01)
  *A61C 13/087* (2006.01)
  *A61C 13/09* (2006.01)
  *A61K 6/00* (2006.01)
  *A61K 6/087* (2006.01)
  *B33Y 80/00* (2015.01)
  *B29C 64/165* (2017.01)
  *B29L 31/00* (2006.01)
  *B28B 1/00* (2006.01)

(52) U.S. Cl.
  CPC ............ *A61C 13/09* (2013.01); *A61K 6/0008* (2013.01); *A61K 6/0073* (2013.01); *A61K 6/083* (2013.01); *A61K 6/087* (2013.01); *A61K 6/0835* (2013.01); *B29C 64/165* (2017.08); *B33Y 30/00* (2014.12); *B33Y 70/00* (2014.12); *B33Y 80/00* (2014.12); *B28B 1/001* (2013.01); *B29L 2031/753* (2013.01)

(56) References Cited

U.S. PATENT DOCUMENTS

| | | | |
|---|---|---|---|
| 8,715,832 B2* | 5/2014 | Ederer | B29C 64/165 427/189 |
| 9,643,360 B2* | 5/2017 | Kashani-Shirazi | B29C 64/165 |
| 2003/0055123 A1* | 3/2003 | Kawashima | A61K 6/0023 523/116 |
| 2005/0079086 A1 | 4/2005 | Farr et al. | |
| 2007/0100019 A1* | 5/2007 | Sun | A61K 6/0017 523/116 |
| 2010/0204421 A1* | 8/2010 | Yarimizu | A61K 6/083 526/222 |
| 2010/0291314 A1* | 11/2010 | Kashani-Shirazi | B29C 64/165 427/521 |
| 2011/0076438 A1 | 3/2011 | Farr et al. | |
| 2015/0259247 A1 | 9/2015 | Watanabe | |
| 2016/0038633 A1 | 2/2016 | Watanabe | |

FOREIGN PATENT DOCUMENTS

| | | |
|---|---|---|
| JP | 2004-330743 | 11/2004 |
| JP | 2006-506246 | 2/2006 |
| JP | 2009-102526 | 5/2009 |
| JP | 2016-172333 | 9/2016 |
| WO | WO2004/043681 A2 | 5/2004 |

OTHER PUBLICATIONS

European Office Action dated Nov. 19, 2018 in Patent Application No. 16195156.1, 5 pages.

* cited by examiner

FIG. 1

SOLID FREEFORM FABRICATION MATERIAL SET, METHOD OF FABRICATING SOLID FREEFORM OBJECT, METHOD OF FABRICATING DENTAL PROSTHESIS, AND DEVICE FOR FABRICATING SOLID FREEFORM OBJECT

CROSS-REFERENCE TO RELATED APPLICATIONS

This patent application is based on and claims priority pursuant to 35 U.S.C. § 119 to Japanese Patent Application Nos. 2015-209338 and 2016-182144, filed on Oct. 23, 2015 and Sep. 16, 2016, in the Japan Patent Office, the entire disclosures of which are hereby incorporated by reference herein.

BACKGROUND

Technical Field

The present invention relates to a solid freeform fabrication material set, a method of fabricating a solid freeform object, a method of fabricating a dental prosthesis, and a device for fabricating a solid freeform object.

Description of the Related Art

Dental prosthesis (prosthetic tooth) is typically made of metal materials such as cobalt-chrome alloy, ceramic materials such as zirconia, and organic materials such as hybrid resins made of the ceramic material and resins.

Prosthetic teeth using the organic material containing a cross-linking agent, a reaction promoter, etc. are expected to be much harder than prosthetic teeth including a mono-material of polymethyl methacrylate. In addition, using an organic material such as a hybrid resin including the resin combined with fillers of zirconia, glass, etc. is expected to harden dental prosthesis.

However, when resins are used as the main component for prosthetic teeth, the resin may be thermally decomposed. Therefore, normal laser cannot be used for sintering, which makes it impossible to conduct additive-manufacturing prosthetic teeth. Moreover, color controlling is not possible with laser.

In an attempt to solve these issues, a method of fabricating a solid freeform object is proposed which includes stacking powder layers while applying a binding agent.

SUMMARY

According to the present invention, provided is an improved solid freeform fabrication material set which includes a material A for solid freeform fabrication including a polymerization initiator A and at least one of an organic particle and an inorganic particle and a material B for solid freedom fabrication including a polymerizable compound B

BRIEF DESCRIPTION OF THE SEVERAL VIEWS OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein.

DESCRIPTION OF THE EMBODIMENTS

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

As used herein, the singular forms "a", "an", and "the" are intended to include the plural forms as well, unless the context clearly indicates otherwise.

Moreover, image forming, recording, printing, modeling, etc. in the present disclosure represent the same meaning.

The present disclosure provides a solid freeform fabrication material set by which complex three-dimensional objects can be easily and efficiently fabricated and the obtained object has good strength immediately after fabrication.

Solid Freeform Fabrication Material Set

The solid freeform fabrication material set (also referred to as additive manufacturing material set) of the present disclosure includes a material A for solid freeform fabrication (also referred to as material A for additive manufacturing), a material B for solid freeform fabrication (also referred to as material B for additive manufacturing), and other optional materials. The material A includes a polymerization initiator A and an organic particle and/or an inorganic particle. The material B includes a polymerizable compound B.

The solid freeform fabrication material set of the present disclosure is based on the knowledge that when a conventional method of manufacturing a 3D fabrication object is used, a binding agent does not react soon or is not dissolved, so that it takes a long time before the 3D fabrication object can be taken out from a device after additive manufacturing and when a binding agent (resin) is used, the binding agent cannot be removed since no sintering is conducted so that it remains as a foreign object.

Material A for Solid Freeform Fabrication (Material A for Additive Manufacturing)

The material A for solid freeform fabrication (material A for additive manufacturing) includes a polymerization initiator A, an organic particle and/or an inorganic particle, and other optional materials. The material A for solid freeform fabrication can be liquid or powder to suit to a particular application.

When the material A for solid freeform fabrication is liquid, the material A preferably further includes a polymerizable compound A.

"Liquid" means the state of the material for solid freeform fabrication at 25 degrees C. is liquid or flowable, which includes slurry.

Organic Particle

Materials of the organic particle have no particular limitation and can be selected to suit to a particular application. Specific examples thereof include, but are not limited to, polymethyl methacrylate (also referred to as PMMA), polycarbonate (also referred to as PC), polyester (also referred to as PES), polyamide such as polyamide 12 (also referred to as PA12), and polyether ether ketone (also referred to as PEEK). The mass average molecular weight of each polymer can be small to large to suit to a particular application.

These can be used alone or in combination. Polyamide 12 has 12 carbon atoms, prepared by ring-opening polycondensation of lauryl lactam.

The mass average molecular weight (Mw) of the organic particle is preferably 100,000 to 1,500,000. When the mass average molecular weight is not less than 100,000, a composition in paste form prepared by swelling of the organic particle is prevented from being excessively soft and it is possible to suitably conduct fabrication of an object. When the mass average molecular weight is not greater than 1,500,000, swelling of the organic particle is accelerated, thereby improving the fabrication speed.

With regard to the mass average molecular weight, for example, it can be calculated based on the molecular weight distribution of separated organic particles obtained by gel permeation chromatography (GPC).

The volume average particle diameter (Dv) of the organic particle is preferably less than 1 μm when the material A for solid freeform fabrication is liquid (dispersion). When the volume average particle diameter (Dv) of the liquid material A is less than 1 μm, dispersed organic particles do not easily precipitate so that formed slurry layers can be uniform. When the material A for solid freeform fabrication is powder, the volume average particle diameter (Dv) is preferably 1-10 μm. When the volume average particle diameter is not less than 1 μm, the swelling speed can be slowed down, so that the reaction does not complete before the material B for solid freeform fabrication permeates into the bottom layer. In addition, fluidity can be improved regardless of the kind of organic particles and powder conveyance is good. When the volume average particle diameter is not greater than 100 μm, the manufacturing accuracy is improved.

With regard to the volume average particle diameter, it can be measured by using a known particle size measuring instrument, for example, Multisizer III (manufactured by Beckman Coulter, Inc.) and FPIA-3000 (manufactured by Sysmex Corporation) according to a known method.

The proportion of the organic particle is preferably 20-70 percent by mass and more preferably 30-50 percent by mass to the total amount of the material A for solid freeform fabrication when it is liquid. On the other hand, the proportion of the organic particle is preferably 80-99 percent by mass and more preferably 90-99 percent by mass to the total amount of the material A for solid freeform fabrication when it is powder.

Inorganic Particle

The inorganic mineral has no specific limitation and is suitably selected to suit to a particular application. For example, zirconia, alumina, silica, and silicate are usable. These can be used alone or in combination.

A specific example of silicate is lithium disilicate.

When the inorganic particle includes zirconia, yttria serving as a sintering helping agent and alumina as a foreign object may be contained.

The proportion of zirconia is preferably not less than 90 percent by mass and more preferably 94 percent by mass to the total amount of the inorganic particle. When the proportion of zirconia is not less than 90 percent by mass, the proportion of foreign object relatively lowers so that the inorganic particle mechanically becomes strong and tends to be colorfast.

The proportion of yttria is preferably 2-6 percent by mass and more preferably 3-5 percent by mass to the total amount of the inorganic particle. Yttria demonstrates sufficient features as a sintering helping agent within the range of 2-6 percent by mass and prevents cracking during sintering.

The proportion of alumina as the foreign object is preferably not greater than 3 percent by mass and more preferably not greater than 1 percent by mass to the total amount of the inorganic particle. When alumina is not greater than 3 percent by mass, it demonstrates good features as the sintering helping agent, affecting little to the color.

The inorganic particle is available on the market. Specific examples include, but are not limited to, product name 3YZ-E (manufactured by TOSOH CORPORATION) as zirconia, product name AHP200 (manufactured by Nippon Light Metal Company Ltd.) as alumina, and product name H201 (manufactured by ASAHI GLASS CO., LTD.) as silica.

The content of zirconia, yttria, and alumina in the inorganic particle can be measured by, for example, inductively coupled plasma (ICP) atomic emission spectrochemical analysis.

The volume average particle diameter (Dv) of the inorganic particle is preferably less than 1 μm when the material A for solid freeform fabrication is liquid (dispersion). When the volume average particle diameter (Dv) of the liquid material A is less than 1 μm, dispersed organic particles do not easily precipitate so that formed slurry layers can be uniform. When the material A for solid freeform fabrication is powder, the volume average particle diameter (Dv) is preferably 1-10 μm. When the volume average particle diameter is not less than 1 μm in the powder state of the material A, fluidity can be improved and powder conveyance becomes good. When the volume average particle diameter is not greater than 100 μm, fabrication accuracy can be improved.

With regard to the volume average particle diameter, it can be measured by using a known particle size measuring instrument, for example, Multisizer III (manufactured by Beckman Coulter, Inc.) and FPIA-3000 (manufactured by Sysmex Corporation) according to a known method.

The method of manufacturing the inorganic particle has no specific limitation and is suitably selected to suit to a particular application. For example, a thermal decomposition technique, a coprecipitation technique, a hydrolysis method, and a synthesis method from a metal salt aqueous solution of, zirconia, yttria, etc. Of these, the thermal decomposition technique and the coprecipitation technique are preferable.

In the thermal decomposition technique, a predetermined amount of oxyzirconium chloride and an aqueous solution of yttria chloride is mixed and the mixture is admixed with sodium chloride (or potassium chloride). The proportion of sodium chloride is 0.1-1 percent by mass to the total amount of oxyzirconium chloride. This liquid mixture is subjected to instant drying such as spray-drying technique to obtain dried powder.

The instant drying is a technique of drying an article within 10 seconds, which is preferably conducted at 200 degrees C. or higher in heated atmosphere.

Next, the dried powder is thermally decomposed in air in the temperature range of 800-1,200 degrees C. to obtain temporarily-baked powder of oxide. The temporarily-baked powder of oxide is pulverized by a wet pulverization method until the pulverization diameter is reduced to 2 μm or less and washed with water. There is no specific limitation to the washing with water. It can be selected to suit to a particular application. For example, a continuous washing filtration method using membrane filters is preferable.

Due to the washing with water, the concentration of sodium (or potassium) in the organic particle is reduced to the range of 10-100 ppm in oxide conversion. The slurry obtained after the washing with water is dried to obtain inorganic particles (zirconia powder).

In the coprecipitation technique, oxyzirconium chloride and yttria chloride aqueous solution are mixed. In particular, to form a metal complex to keep pH at which each hydrate of oxyzirconium chloride and yttria chloride precipitates, sodium sulfate (or potassium sulfate) is added in such a manner that the molar ratio of sodium sulfate (or potassium sulfate) to zirconia is 0.3-0.7 followed by reaction at 50-100 degrees C. for several hours or more. Alkali aqueous solution of sodium hydroxide, ammonium, etc. is added to this mixture while stirring the aqueous solution to set pH of the solution in the range of 8-10. The thus-obtained coprecipitation hydrate particle is sufficiently washed to confirm that sodium (or potassium) in oxide conversion is 10-100 ppm. The hydrate particulates after washing with water is dehydrated and dried and thereafter sintered in the air at the temperature range of 800-1,200 degrees C. to obtain temporarily-sintered powder of oxide. The thus-obtained temporarily-sintered powder of oxide is wet-pulverized to the size of 2 μm or less and dried to obtain inorganic particles (zirconia powder).

The proportion of the inorganic particle is preferably 20-70 percent by mass and more preferably 30-50 percent by mass to the total amount of the material A for solid freeform fabrication when it is liquid. On the other hand, the proportion of the organic particle is preferably 50-99 percent by mass and more preferably 80-95 percent by mass to the total amount of the material A for solid freeform fabrication when it is powder.

Polymerization Initiator A

Examples of the polymerization initiator A are peroxides and tertiary amines.

When the material A for solid freeform fabrication includes a peroxide, it is preferable that the material B for solid freeform fabrication contains a tertiary amine. If peroxide and tertiary amine are separately included in the material A for solid freeform fabrication and the material B for solid freeform fabrication, when the material A for solid freeform fabrication and the material B for solid freeform fabrication are mixed, radical reaction starts. As a result, a compound of the polymerized polymerizable compound A and the organic particle and/or the inorganic particle is obtained.

At this time, since no external energy such as light and heat is required and the compound is obtained immediately after the material A for solid freeform fabrication and the material B for solid freeform fabrication are mixed, it is advantageous that a solid freeform object is simply and efficiently obtained.

Examples of the peroxides are diacyl peroxides including an aromatic series and peroxy esters such as perbenzoic acid esters. Specific examples include, but are not limited to, benzoyl peroxide (BPO), 2,4-dicylorobenzoyl peroxide, m-tolyl peroxide, t-butyl peroxy benzoate, di-t-butyl peroxy isophthalate, and 2,5-dimethyl-2,5-di(benzoylperoxy) hexane. These can be used alone or in combination. Of these, benzoyl peroxide (BPO) is preferable.

There is no specific limitation to the method of adding the peroxide. It is suitable to uniformly mix the peroxide with the organic particle and/or inorganic particle or disperse the peroxide in the organic particle and/or inorganic particle. When the peroxide is solid at room temperature, it is suitable to mix the peroxide with the organic particle and/or inorganic particle or disperse the peroxide in the organic particle and/or inorganic particle. When the peroxide is mixed with the organic particle and/or inorganic particle, it is preferable to use a HENSCHEL MIXER or utilize air blow for mixing. It is preferable that these devices be made of stainless steel (SUS).

In addition, when the organic particle is used, the organic particle is synthesized by emulsion polymerization and thereafter a suitable amount of the peroxide is added thereto to obtain a master batch. When the peroxide is liquid at room temperature, it is necessary to permeate the peroxide into the organic particle. That permeation of a suitable amount of the peroxide can suppress deterioration of flowability of powder, preventing the powder from being not conveyed.

The proportion of the peroxide is preferably 1-5 parts by mass and more preferably 1-3 parts by mass to 100 parts by mass of the organic particle and/or the inorganic particle. When the content is 1 part by mass or more, the radical reaction rapidly proceeds so that a solid freeform object can be obtained at a desired speed. Also, the mechanical strength of the solid freeform object can be improved. When the content is 5 part by mass or less, it is possible to prevent agglomeration (block) of the peroxide, uniformly disperse the peroxide in the particle, and prevent occurrence of noise of explosion and uneven strength during radical reaction. In addition, yellow discoloration can be suppressed.

The content of the polymerization initiator A is preferably 1-5 parts by mass and more preferably 1-3 parts by mass to 100 parts by mass of the material A for solid freeform fabrication. When the content is 1 part by mass or more, the radical reaction rapidly proceeds so that a solid freeform object can be obtained at a desired speed. Also, the mechanical strength of the solid freeform object can be improved. When the content is 5 part by mass or less, it is possible to prevent agglomeration (block) of the peroxide, uniformly disperse the peroxide in the particle, and prevent occurrence of noise of explosion and uneven strength during radical reaction. In addition, yellow discoloration can be suppressed.

Other Polymerization Initiator

As other polymerization initiators, for example, room temperature polymerization initiators can be used in combination with the peroxide.

Examples of the room temperature polymerization initiators are pyrimidine trione derivatives, organic metal compounds, and organic halogen compounds. Of these, when a pyrimidine trione derivative and an organic metal compound are included in the material A for solid freeform fabrication, it is preferable for the material B for solid freeform fabrication to include an organic halogen compound. When an organic halogen compound is included in the material A for solid freeform fabrication, it is preferable for the material B for solid freeform fabrication to include a pyrimidine trione derivative and an organic metal compound.

Specific examples of the pyrimidine trione derivative include, but are not limited to, 1-cyclohexyl-5-ethylpyrimidine trione, 1-benzyl-5-phenylpyrimidine trione, 5-butylpyrimidine trione, 5-phenylpyrimidine trione, 1,3-dimethylpyrimidine trione, and 5-ethylpyrimidine trione. These can be used alone or in combination.

Specific examples of the organic metal compound include, but are not limited to, copper acetylacetonate, 4-cyclohexyl copper lactate, copper(II) acetate, copper oleate, manganese acetylacetonate, manganese naphthenate, manganese octoate, cobalt acetylacetonate, cobalt naphthenate, lithium acetylacetonate, lithium acetate, zinc acetylacetonate, zinc naphthenate, nickel acetylacetonate, nickel acetate, aluminium acetylacetonate. calcium acetylacetonate, chrome acetylacetonate, iron acetylacetonate, sodium naphthenate, and rear earth octoate. These can be used alone or in combination.

Specific examples of the organic halogen compound include, but are not limited to, dilauryldimethylammonium chloride, lauryldimethylammonium chloride, tetra-n-butylammonium chloride, trioctylmethylammonium chloride, benzyldimethylcetyl ammonium chloride, and benzyldimethylstearylammonium chloride. These can be used alone or in combination.

Polymerizable Compound A

It is preferable that the polymerizable compound A be contained in the material A for solid freeform fabrication when the material A for solid freeform fabrication is liquid.

The polymerizable compound A has no specific limitation and is suitably selected to suit to a particular application as long as the polymerizable compound A has a certain degree of viscosity. For example, a polymerizable compound having a vinyl group is suitable.

Examples of the polymerizable compound having a vinyl group are mono-functional polymerizable compounds and poly-functional polymerizable compounds. These can be used alone or in combination. Of these, it is preferable to use the mono-functional compounds and poly-functional compounds in combination to impart thickening effect. The mono-functional compounds and poly-functional compounds can be mixed or can be chemically bonded with each other to form an oligomer.

Mono-functional Polymerizable Monomer

Examples of the mono-functional polymerizable compound are mono-functional acrylic compounds and mono-functional methacrylic compounds. These can be used alone or in combination. Of these, mono-functional methacrylic compounds are preferable and mono-functional methacrylic compounds having a methyl methacrylate backbone are more preferable.

Specific examples of the mono-functional methacrylic compounds having a methyl methacrylate backbone include, but are not limited to, alkyl methacrylates such as methyl methacrylate (MMA), ethyl methacrylate, isopropyl methacrylate, t-butyl methacrylate, n-butyl methacrylate, isobutyl methacrylate, buthoxyethyl methacrylate, and 2-ethylhexyl methacrylate; hydroxyalkyl methacrylate (HAMA) such as 2-hydroxyethyl methacrylate (HEMA), 3-hydroxy propyl methacrylate, 2-hydroxy-1,3-dimethacryloxy propane, and hydroxy propyl methacrylate; tetrahydro furfuryl methacrylate, glycidyl methacrylate, ethylene glycol methacrylate, 2-methoxyethyl methacrylate, and benzyl methacrylate. These can be used alone or in combination. Of these, in terms of a balance with breakage toughness of a prosthesis, it is preferable to use methyl methacrylate (MMA) and hydroxy alkyl methacrylate (HAMA) in combination and more preferable to use a combination of methyl methacrylate (MMA) and 2-hydroxyethyl methacrylate (HEMA).

The number of carbon atoms in the alkyl chain of the hydroxy alkyl methacrylate (HAMA) is preferably 2-4. When the number of carbon atoms is 2-4, mechanical strength is improved.

The proportion of the hydroxy alkyl methacrylate is preferably 10-30 parts by mass and more preferably 15-25 parts by mass to 100 parts by mass of the liquid material. When the content is not less than 10 parts by mass, breakage toughness is good, thereby preventing breakage of a prosthesis in a mouth. When the content is not greater than 30 parts by mass, bending strength is improved, thereby preventing breakage of a prosthesis in a mouth.

The proportion of the mono-functional polymerizable compound is preferably 30-80 parts by mass and more preferably 40-70 parts by mass to 100 parts by mass of the material A for solid freeform fabrication. When the content is not less than 30 parts by mass, viscosity of the liquid lowers so that the liquid layer can be easily formed by a doctor blade, etc. When the content is not greater than 80 parts by mass, bending strength is improved, thereby preventing breakage of a prosthesis in a mouth.

Poly-functional Polymerizable Compound

Examples of the poly-functional polymerizable compound are poly-functional acrylic compounds and poly-functional methacrylic compounds. Of these, poly-functional methacrylic compounds are preferable and poly-functional methacrylic compounds having a methyl methacrylate backbone are more preferable.

Specific examples of the poly-functional methacrylic compounds having a methyl methacrylate backbone include, but are not limited to, diethylene glycol dimethacrylate, 1,3-butyleneglycol dimethacrylate, 1,4-butyleneglycol dimethacrylate, tetraethyleneglycol dimethacrylate (TEGDMA), urethane dimethacrylate (UDMA), and bisphenol A diglycidyl methacrylate (Bis-GMA). These can be used alone of in combination. Of these, urethane dimethacrylate (UDMA) and bisphenol A diglycidyl methacrylate (Bis-GMA), which have a high viscosity, are preferable and bisphenol A diglycidyl methacrylate (Bis-GMA) is more preferable.

The proportion of at least one of the poly-functional acrylic compound and the poly-functional methacrylic compound is preferably 30-80 parts by mass and more preferably 40-70 parts by mass to 100 parts by mass of the material A for solid freeform fabrication. When the content is not less than 30 parts by mass, it is possible to make an adjustment at a desired viscosity so that the liquid layer formed by a doctor blade does not easily flow and stably stay at a desired position. When the content is not greater than 80 parts by mass, increase of non-reacted components can be suppressed, thereby preventing breakage of a prosthesis in a mouth ascribable to deterioration of mechanical strength.

Other Components

The other optional components are not particularly limited and can be selected to suit to a suitable application. Examples thereof are a fluidizer and a filler. When the material A for solid freeform fabrication is powder, an addition of a fluidizer thereto is preferable to easily and efficiently form layers, etc. of the material A for solid freeform fabrication. Also, it is preferable to include a filler because voids etc. do not easily appear in an obtained cured object.

Property of Material A for Solid Freeform Fabrication

Viscosity at 25 degrees C. of the material A for solid freeform fabrication when the material A for solid freeform fabrication is liquid is preferably 50-200 mPa·s. When the viscosity is 50-200 mPa·s, the material A for solid freeform fabrication can be stably discharged so that the dimension accuracy and mechanical strength of a solid freeform object can be improved. Viscosity can be measured according to JIS-K7117. Also, it can be measured at 25 degrees C. by a B type rotation viscometer (TVB-10M, manufactured by TOKI SANGYO CO., LTD.).

Material B for Solid Freeform Fabrication (Material B for Additive Manufacturing)

The material B for solid freeform fabrication (material B for additive manufacturing) includes the polymerizable compound B and optionally a polymerization initiator B and other materials.

The material B for solid freeform fabrication is preferably liquid.

Polymerizable Compound B

The polymerizable compound B has no specific limitation and is suitably selected to suit to a particular application. For example, a polymerizable compound having a vinyl group is suitable.

Examples of the polymerizable compound having a vinyl group are mono-functional polymerizable compounds and poly-functional polymerizable compounds. Of these, it is preferable to use the mono-functional compounds and poly-functional compounds in combination. The mono-functional compounds and poly-functional compounds can be mixed or can be chemically bonded with each other to form an oligomer.

Mono-functional Polymerizable Monomer

Examples of the mono-functional polymerizable compound are mono-functional acrylic compounds and mono-functional methacrylic compounds. Of these, mono-functional methacrylic compounds are preferable and mono-functional methacrylic compounds having a methyl methacrylate backbone are more preferable.

Specific examples of the mono-functional compounds include, but are not limited to, alkyl methacrylates such as methyl methacrylate (MMA), ethyl methacrylate, isopropyl methacrylate, t-butyl methacrylate, n-butyl methacrylate, isobutyl methacrylate, buthoxyethyl methacrylate, and 2-ethylhexyl methacrylate; hydroxyalkyl methacrylate (HAMA) such as 2-hydroxyethyl methacrylate (HEMA), 3-hydroxy propyl methacrylate, and hydroxy propyl methacrylate; tetrahydro furfuryl methacrylate, glycidyl methacrylate, ethylene glycol methacrylate, 2-methoxyethyl methacrylate, and benzyl methacrylate. These can be used alone or in combination. Of these, in terms of a balance with breakage toughness of a prosthesis, it is preferable to use methyl methacrylate (MMA) and hydroxy alkyl methacrylate (HAMA) in combination and more preferable to use a combination of methyl methacrylate (MMA) and 2-hydroxyethyl methacrylate (HEMA).

The number of carbon atoms in the alkyl chain of hydroxy alkyl methacrylate (HAMA) is 2-4. When the number of carbon atoms is 2-4, mechanical strength is improved.

The proportion of the mono-functional polymerizable compound is preferably 10-30 parts by mass and more preferably 15-25 parts by mass to 100 parts by mass of the material B for solid freeform fabrication. When the content is not less than 10 parts by mass, breakage toughness is good, thereby preventing breakage of a prosthesis in a mouth. When the content is not greater than 30 parts by mass, bending strength is improved, thereby preventing breakage of a prosthesis in a mouth.

The proportion of the hydroxy alkyl methacrylate is preferably 10-30 parts by mass and more preferably 15-25 parts by mass to 100 parts by mass of the material B for solid freeform fabrication. When the content is not less than 10 parts by mass, breakage toughness is good, thereby preventing breakage of a prosthesis in a mouth. When the content is not greater than 30 parts by mass, bending strength is improved, thereby preventing breakage of a prosthesis in a mouth.

Poly-functional Polymerizable Compound

Examples of the poly-functional polymerizable compound are poly-functional acrylic compounds and poly-functional methacrylic compounds. Of these, poly-functional methacrylic compounds are preferable and poly-functional methacrylic compounds having a methyl methacrylate backbone are more preferable.

Specific examples of the poly-functional compound include, but are not limited to, diethylene glycol dimethacrylate, 1,3-butylene glycol dimethacrylate, 1,4-butylene glycol dimethacrylate, tetraethylene glycol dimethacrylate (TEGDMA), urethane dimethacrylate (UDMA), bisphenol A diglycidyl methacrylate (Bis-GMA), and 2-hydroxy-1,3-dimethacryloxy propane. These can be used alone or in combination. Of these, tetraethylene glycol dimethacrylate (TEGDMA), urethane dimethacrylate (UDMA), and bisphenol A diglycidyl methacrylate (Bis-GMA) are preferable and bisphenol A diglycidyl methacrylate (Bis-GMA) is more preferable.

The proportion of the mono-functional polymerizable compound is preferably 10-30 parts by mass and more preferably 15-25 parts by mass to 100 parts by mass of the material B for solid freeform fabrication. When the content is not less than 10 parts by mass, mechanical strength is improved, thereby preventing breakage of a prosthesis in a mouth. When the content is not greater than 30 parts by mass, increase of non-reacted components can be suppressed, thereby preventing breakage of a prosthesis in a mouth caused by deterioration of mechanical strength.

The proportion of the poly-functional acrylic compound and/or the poly-functional methacrylic compound is preferably 10-30 parts by mass and more preferably 15-25 parts by mass to 100 parts by mass of the liquid material. When the content is not less than 10 parts by mass, mechanical strength is improved, thereby preventing breakage of a prosthesis in a mouth. When the content is not greater than 30 parts by mass, increase of non-reacted components can be suppressed, thereby preventing breakage of a prosthesis in a mouth caused by deterioration of mechanical strength.

Polymerization Initiator B

As for the polymerization initiator B, the same materials as those for the material A for solid freeform fabrication can be used.

When the material A for solid freeform fabrication includes a peroxide as the polymerization initiator A, it is preferable that the material B for solid freeform fabrication includes a tertiary amine as the polymerization initiator B.

The tertiary amine preferably has a structure in which a nitrogen atom is directly substituted in an aromatic group and more preferably has a toluidine backbone.

Specific examples of the tertiary amine having a toluidine backbone include, but are not limited to, N,N-dimethyl-p-toluidine (DMPT), N,N-diethyl-p-toluidine (DEPT), N,N-di(β-hydroxyethyl)-p-toluidine, and N,N-di(β-hydroxypropyl)-p-toluidine. These can be used alone or in combination. Of these, N,N-dimethyl-p-toluidine (DMPT) and N,N-diethyl-p-toluidine (DEPT) are preferable and N,N-dimethyl-p-toluidine (DMPT) is more preferable.

The proportion of the tertiaryl amine is preferably 1-5 parts by mass and more preferably 1.5-3 parts by mass to 100 parts by mass of the material B for solid freeform fabrication. When the content is 1 part by mass or more, the radical reaction rapidly proceeds so that a solid freeform object can be obtained at a desired speed. When the content is 5 parts by mass or less, yellow discoloration of a solid freeform object can be suppressed.

The content of the polymerization initiator B is preferably 1-5 parts by mass and more preferably 1.5-3 parts by mass to 100 parts by mass of the material B for solid freeform fabrication. When the content is 1 part by mass or more, the radical reaction rapidly proceeds so that a solid freeform object can be obtained at a desired speed. When the content is 5 parts by mass or less, yellow discoloration of a solid freeform object can be suppressed.

Other Polymerization Initiator

As for the polymerization initiator, the same polymerization initiators as those for the material A for solid freeform fabrication can be used.

Other Components

The other components are selected taking into account the conditions such as the kind of device to apply the material B for solid freeform fabrication, frequency of usage, and quantity. For example, it is possible to select the other component considering the impact of clogging in a liquid discharging head in an inkjet printer, etc. Examples thereof are organic solvents, viscosity modifiers, pigments, and stabilizing agents.

The organic solvent is, for example, alcohols such as ethanol, ethers, and ketones. Of these, ethanol is preferable.

Property of Material B for Solid Freeform Fabrication

Viscosity at 25 degrees C. of the material B for solid freeform fabrication is preferably 4-20 mPa·s and more preferably 5-8 mPa·s. When the viscosity is 4-20 mPa·s, the material B for solid freeform fabrication can be stably discharged so that the dimension accuracy and mechanical strength of a solid freeform object can be improved. Viscosity can be measured according to JIS-K7117. Also, it can be measured at 25 degrees C. by a B type rotation viscometer (TVB-10M, manufactured by TOKI SANGYO CO., LTD.).

The surface tension of the material B for solid freeform fabrication is preferably 50 mN/m or less and more preferably 30 mN/m or less. When the viscosity is not greater than 50 mPa·s, the material B for solid freeform fabrication can be stably discharged so that the dimension accuracy of a solid freeform object is good and mechanical strength thereof can be improved.

Method of Fabricating Solid Freeform Object (Additive Manufacturing Object), Device for Fabricating Solid Freeform Object (Additive Manufacturing Object), Method of Fabricating Dental Prosthesis, and Device for Fabricating Dental Prosthesis The method of fabricating a solid freeform object (additive manufacturing object) of the present disclosure includes forming a layer, applying the material B, and other optional processes.

The device for fabricating a solid freeform object (additive manufacturing object) of the present disclosure includes a layer-forming device, a material B application device, and other optional devices.

The method of fabricating a dental prosthesis of the present disclosure includes forming a layer, applying the material B, and other optional steps.

The device for fabricating a dental prosthesis includes a layer-forming device, a material B application device, and other optional devices.

The method of fabricating a solid freeform object (additive manufacturing object) of the present disclosure can be suitably conducted by the device for fabricating the solid freeform object (additive manufacturing object). The process of forming a layer can be suitably conducted by the layer forming device and the process of applying the material B is suitably conducted by the material B applying device. The other optional processes can be executed by the other optional devices.

The method of fabricating a dental prosthesis of the present disclosure can be suitably conducted by the device for fabricating a dental prosthesis. The process of forming a layer can be suitably conducted by the layer forming device and the process of applying the material B is suitably conducted by the material B applying device. The other optional processes can be executed by the other optional devices.

Layer Forming Process and Layer Forming Device

In the layer forming process, a layer of the material A for solid freeform fabrication is formed using the material A for solid freeform fabrication in the solid freeform fabrication material set of the present disclosure.

The layer foiling device forms a layer of the material A for solid freeform fabrication using the material A for solid freeform fabrication in the solid freeform fabrication material set of the present disclosure.

Formation of Material A for Solid Freeform Fabrication

The method of placing the material A for solid freeform fabrication on a substrate is not particularly limited and can be suitably selected to suit to a particular application. For example, a method using a known counter rotation mechanism (counter roller) for use in a selective laser sintering method, a method of extending the material A for solid freeform fabrication to a thin layer using a member such as a brush, a roller, or a blade, a method of pressing the surface of the material A for solid freeform fabrication using a pressure member to extend the material A for solid freeform fabrication to a thin layer, and a method of using a known additive manufacturing device are suitable as the method of placing the material A for solid freeform fabrication in a thin layer.

Substrate

The substrate is not particularly limited and can be suitably selected to suit to a particular application. Preferably, the substrate can place the material A for solid freeform fabrication thereon. For example, a known platform or base plate having a surface on which the material A for solid freeform fabrication is placed is suitably used. The surface of the substrate, that is, the surface on which the material A for solid freeform fabrication is placed can be smooth, coarse, plane, or curved.

Using the counter rotation mechanism (counter roller), the brush, the blade, or the pressing member, a thin layer of the material A for solid freeform fabrication can be formed on the substrate, for example, in the following manner: For example, in an outer frame (also referred to as "form", "hollow cylinder", "tubular structure", etc.), the material A for solid freeform fabrication is placed onto the substrate arranged to move up and down slidably along the inside wall of the outer frame by the counter rotation mechanism (counter roller), the brush, the blade, the pressing member, etc. At this point, if a substrate movable up and down in the outer frame is used, the substrate can be arranged slightly lower than the upper opening of the outer frame. That is, while placing the substrate with an amount corresponding to the layer thickness of the material A for solid freeform in fabrication lower than the upper hole, the material A for solid freeform fabrication is placed on the substrate. As a result, a thin layer of the material A for solid freeform fabrication can be placed on the substrate.

When the material B for solid freeform fabrication is applied to the thin layer of the material A for solid freeform fabrication placed on the substrate, the thin layer is cured. Thereafter, if the material A for solid freeform fabrication is placed on the cured thin layer in the same manner as described above and the material B for solid freeform fabrication is applied to the material A for solid freeform fabrication placed on the thin layer, curing occurs. That curing occurs not only at the material A for solid freeform fabrication formed on the thin layer but also the border between the cured material layer and the thin layer (cured object) that is already cured and present below the cured material. As a consequence, a cured object (solid freeform object, object produced by additive manufacturing) is obtained which has a thickness corresponding to about the two layers of the material A for solid freeform fabrication.

In addition, it is possible to automatically and simply place a thin layer of the material A for solid freeform fabrication on the substrate mentioned above by the known additive manufacturing device described above. The known additive manufacturing device includes a recoater to laminate the material A for solid freeform fabrication, a movable supplying tank to supply the material A for solid freeform fabrication onto the substrate mentioned above, and a movable modeling tank to laminate thin layers of the material A for solid freeform fabrication. In the additive manufacturing device, the supplying tank is elevated, the modeling tank is elevated down, or both to set the surface of the supplying tank slightly above the surface of the modeling tank. In addition, the material A for solid freeform fabrication is arranged to form a thin layer using the recoater from the supplying tank side and the recoater is repetitively moved to laminate thin layers of the material A for solid freeform fabrication.

The thickness of the material A for solid freeform fabrication is not particularly limited and can be selected to suit to a particular application. For example, the average thickness per layer is preferably 10-70 μm and more preferably 20-50 μm when the material A for solid freeform fabrication is liquid. When the average thickness is not less than 10 μm, it does not take a long time before a solid freeform object is obtained. When the average thickness is not greater than 70 μm, the dimension accuracy of a solid freeform object can be improved. On the other hand, when the material A for solid freeform fabrication is powder, for example, the average thickness per layer is preferably 10-200 μm and more preferably 50-150 μm. When the average thickness is not less than 10 μm, it does not take a long time before a solid freeform object is obtained. When the average thickness is not greater than 200 μm, the dimension accuracy of a solid freeform object can be improved. The average thickness can be measured by a known method.

Process of Applying Material B and Device for Applying Material B

In the process of applying the material B, the material B for solid freeform fabrication in the solid freeform fabrication material set of the present disclosure is applied to the layer of the material A for solid freeform fabrication.

The device for applying the material B applies the material B for solid freeform fabrication in the solid freeform fabrication material set of the present disclosure to the layer of the material A for solid freeform fabrication.

The device of applying the material B for solid freeform fabrication to a layer of the material A for solid freeform fabrication has no particular limitation and can be selected to suit to a particular application. For example, liquid discharging devices for use in a dispenser method, a spray method, or an inkjet method are suitable. In the present disclosure, the liquid discharging device for use in the inkjet method (which uses an oscillator such as a piezoelectric actuator to discharge droplets from multiple nozzles) is preferable in terms that complex solid freeform objects can be efficiently and precisely fabricated.

Other Processes and other Devices

The other processes include a surface protection treatment process, a coating (application) process, etc.

The other devices include a surface protection treatment device, a coating (application) device, etc.

Surface Protection Process and Surface Protection Device

The surface protection treatment process is to form a protection layer on a solid freeform object fabricated in the process of applying the material B. Due to the surface protection treatment process, durability is imparted to the surface of the solid freeform object to the degree that, for example, the object can be used as is. Specific examples of the protection layer include, but are not limited to, a water-resistance layer, a weather resistance layer, a light resistance layer, a heat insulation layer, and a gloss layer. Specific examples of the surface protection treatment device include, but are not limited to, known surface protection treatment devices such as a spraying device and a coating device.

Coating Process and Coating Device

The coating (application) process is to coat the solid freeform object. Due to this coating process, the solid freeform object is colored in a desired color.

Specific examples of the coating device include, but are not limited to, known coating devices using a spray, a roller, a brush, etc.

Figure 1:
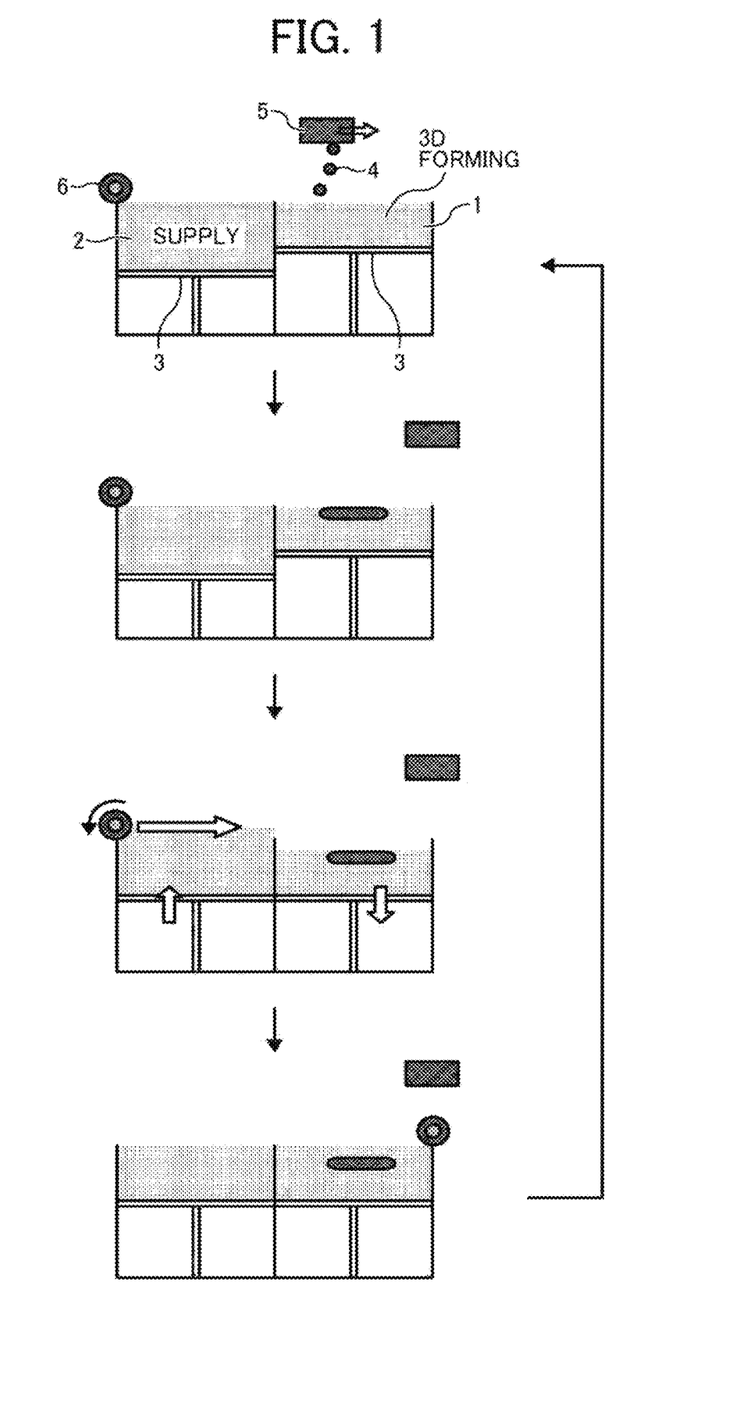
FIG. 1 is a schematic diagram illustrating an example of the device for fabricating a solid freeform object according to an embodiment of the present invention.

FIG. 1 is a diagram illustrating an example of the device for fabricating a solid freeform object of the present disclosure. The device for fabricating a solid freeform object illustrated in FIG. 1 includes a material storage tank 1 on the solid freeform object fabrication side and a material storage tank 2 on the material supplying side, each of these material storage tanks storing the material A for solid freeform fabrication. The device further includes a stage 3 movable up and down and forms layers fowled of the material A for solid freeform fabrication.

The device for fabricating a solid freeform object has an inkjet head 5 over the material storage tank 1 to discharge the material B 4 for solid freeform fabrication toward the material A for solid freeform fabrication in the material storage tank 1. Moreover, the device for fabricating a solid freeform fabrication also has a smoothing mechanism (hereinafter also referred to as recoater) 6 to supply the material A for solid freeform fabrication from the material storage tank 2 to the material storage tank 1 and smooth the surface of the layer of the material A for solid freeform fabrication in the material storage tank 1.

The material B 4 for solid freeform fabrication is dripped from the inkjet head 5 onto the material A for solid freeform fabrication in the material storage tank 1. At the time of the dripping, the position where the material B 4 for solid freeform fabrication is dripped is determined by two-dimensional image data (slice data) obtained by slicing a target solid freeform shape into multiple plane layers.

After completing depiction of an amount corresponding to a single layer, the stage 3 for the material storage tank 2 is elevated while the stage 3 for the material storage tank 1 is elevated down. The amount of the material A for solid freeform fabrication corresponding to the difference is moved to the material storage tank 1 on the solid freeform fabrication side by the smoothing mechanism 6.

This is how a new layer of the material A for solid freeform fabrication is formed on the surface of the previously formed layer of the material A for solid freeform fabrication. The thickness per layer of the material A is about several tens μm to about several hundreds μm.

Furthermore, depiction is conducted on the newly-formed layer of the material A for solid freeform fabrication based on slice data for the second layer. This series of processes are repeated to obtain a solid freeform object.

Figure 2:
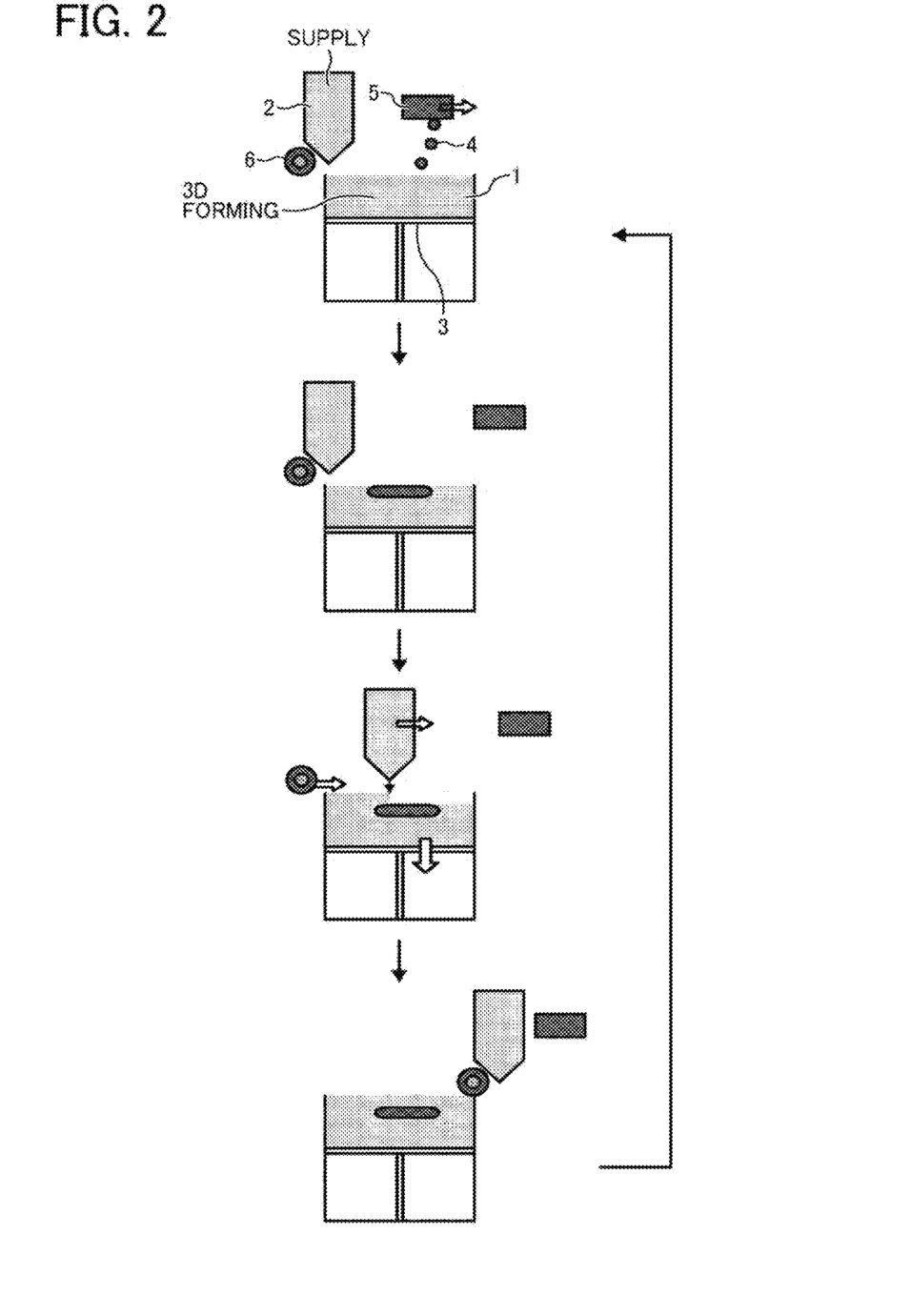
FIG. 2 is a schematic diagram illustrating another example of the device for fabricating a solid freeform object according to an embodiment of the present invention.

FIG. 2 is a diagram illustrating another example of the device for fabricating a solid freeform object of the present disclosure. The device for fabricating a solid freeform object illustrated in FIG. 2 operates on the same principle as that illustrated in FIG. 1. However both have different supplying mechanisms for the material A for solid freeform fabrication. That is, the material storage tank 2 on the supplying side is disposed above the material storage tank 1 on the fabrication side. When the depiction of the first layer is finished, the stage 3 of the material storage tank 1 is lowered in a predetermined amount and the material A for solid freeform fabrication is dropped from the material storage tank 2 on the supplying side to the material powder storage tank 1 on the fabrication side while the material storage tank 2 on the supplying side is moving in order to form a new layer of the material A for solid freeform fabrication layer. Thereafter, the recoater 6 compresses the layer of the material A for solid freeform fabrication to increase the bulk density and also smooths the height of the layer of the material A for solid freeform fabrication.

The material additive manufacturing device illustrated in FIG. 2 can have a compact configuration in size in comparison with the configuration illustrated in FIG. 1 in which the two material storage tanks are arranged in a plane.

Solid Freeform Object (Additive Manufacturing Object) and Dental Prosthesis

The solid freeform object (additive manufacturing object) is fabricated by the method of fabricating a solid freeform object of the present disclosure.

The dental prosthesis is fabricated by the method of fabricating a dental prosthesis of the present disclosure.

The object of the present disclosure can be suitably used as a dental prosthesis.

As for the usage of the dental prosthesis, for example, it can be used as prosthetic tooth, removable partial denture, complete denture, implant, and bridgework.

Bend Stress of Solid Freeform Object

The bending strength of the solid freeform object is preferably 50 MPa or more and more preferably 80 MPa or more. When the bending strength is not less than 50 MPa, the obtained solid freeform object has sufficient strength. The bending strength can be measured by the three-point bending test according to JIS-T-6501 using a desktop precision universal testing machine (AUTOGRAPH-AGS-J, manufactured by Shimadzu Corporation).

Bending Elastic Modulus of Solid Freeform Object

The bending elastic modulus of the solid freeform object is preferably 1.5 GPa or more and more preferably 2.0 GPa or more. When the bending elastic modulus is not less than 1.5 GPa, the obtained solid freeform object has sufficient strength. The bending elastic modulus can be measured by the three-point bending test according to JIS-T-6501 using a desktop precision universal testing machine (AUTO-GRAPH-AGS-J, manufactured by Shimadzu Corporation).

Vickers Hardness of Solid Freeform Object

Vickers hardness of the solid freeform object is preferably 10HV0.2 or more and more preferably 18HV0.2 or more. When the Vickers hardness is not less than 10HV0.2, the obtained solid freeform object has sufficient strength. Vickers hardness can be measured according to JIS-T-6501 by using a Vickers hardness tester (FV-800, manufactured by FUTURE-TECH CORP). Vickers hardness is a value measured at a test force of 0.2 kg.

Amount of Remaining Monomer in Solid Freeform Object

The proportion of remaining monomer in the solid freeform object is preferably not greater than 10 percent by mass, more preferably not greater than 5 percent by mass, and particularly preferably not greater than 1 percent by mass to the total content of the solid freeform object. When the proportion is not greater than 10 percent by mass, foreign materials contained in a solid freeform object can be reduced. Also, strength and dimension accuracy can be improved. The proportion of the remaining monomer in the solid freeform object can be measured according to JIS-T-6501 by using high performance liquid chromatography (HPLC) (LC2010, manufactured by Shimadzu Corporation).

In the present disclosure, in comparison with an additive manufacturing object obtained by a typical additive manufacturing method, solid freeform objects are cured layer by layer so that the amount of the remaining monomer in the obtained solid freeform object is not zero but can be extremely reduced.

According to the fabricating method and the fabricating device, it is possible to simply and efficiently fabricate a solid freeform object having a complex form mainly formed of resins, which demonstrates high level of strength immediately after it is fabricated. Since the thus-obtained solid freeform object has a sufficient strength and excellent dimension accuracy reproducing fine roughness and curved planes, the object has aesthetic aspect with high quality and can be suitably used for various purposes.

Having generally described preferred embodiments of this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Next, embodiments of the present disclosure are described in detail with reference to Examples but not limited thereto.

The volume average particle diameter (Dv) of the organic particle and inorganic particle in the material A for solid freeform fabrication, viscosity of the material A for solid freeform fabrication and the material B for solid freeform fabrication, and the content of the remaining monomer of a solid freeform object are obtained in the following manner.

Volume Average Particle Diameter (Dv) of Organic Particle and Inorganic Particle in Material A for Solid Freeform Fabrication Coulter Multisizer III (manufactured by Beckman Coulter, Inc.) was used as the measuring instrument. An interface (manufactured by Nikkaki Bios Co., Ltd.) to output the number distribution and the volume distribution and a home computer was connected to the instrument. One percent by mass aqueous solution of NaCl was prepared as electrolytic solution using first-class sodium chloride. In the measuring method, 0.1-5 mL of a surfactant (salt of alkylbenzene sulfonic acid) was added as a dispersant to 100 to 150 mL of 1 percent by mass aqueous solution of NaCl as an electrolytic solution. Thereafter, 2-20 mg of the material A for solid freeform fabrication was further added, followed by dispersion treatment by an ultrasonic dispersion device for 1-3 minutes. Furthermore, 100-200 mL of the electrolytic aqueous solution was charged in another beaker. Thereafter, the obtained sample liquid dispersion was charged into the beaker to obtain a predetermined concentration. 50,000 particles were measured using the Coulter Multisizer III with an aperture of 100 μm to obtain the average. In the measuring, the liquid dispersion of the material A for solid freeform fabrication was dripped in such a manner that the concentration indicated by the measuring instrument was 6-10 percent by mass.

Viscosity of Material A for Solid Freeform Fabrication and Material B for Solid Freeform Fabrication Viscosity of the material A for solid freeform fabrication and the material B for solid freeform fabrication was measured at 25 degrees C. by using a B type rotatory viscometer (TVB-10 M, manufactured by TOKI SANGYO CO., LTD.).

Amount of Remaining Monomer in Solid Freeform Object

The amount of the remaining monomer in the solid freeform object was measured by high performance liquid chromatography (HPLC) (LC2010, monomer Shimadzu Corporation).

Preparation Example 1 of Material A for Solid Freeform Fabrication

Preparation Example 1 of Material A1 for Solid Freeform Fabrication 100 parts by mass of polymethyl methacrylate (PMMA, manufactured by KURARAY CO., LTD.) and 1 part by mass of benzoyl peroxide (BPO, manufactured by Tokyo Chemical Industry Co. Ltd.) were mixed by air blow to prepare a powder material A1 for solid freeform fabrication.

Preparation Example 2 of Material A for Solid Freeform Fabrication

Preparation of Material A2 for Solid Freeform Fabrication

Powder material A2 for solid freeform in fabrication was prepared in the same manner as in the preparation of the powder material A1 for solid freeform fabrication except that polymethyl methacrylate (PMMA) was changed to polycarbonate (PC, manufactured by Mitsubishi Engineering-Plastics Corporation).

Preparation Example 3 of Material A for Solid Freeform Fabrication

Preparation of Material A3 for Solid Freeform Fabrication

Powder material A3 for solid freeform fabrication was prepared in the same manner as in the preparation of the powder material A1 for solid freeform fabrication except that polymethyl methacrylate (PMMA) was changed to polyamide 12 (PA12, manufactured by Toray Industries, Inc.).

Preparation Example 4 of Material A for Solid Freeform Fabrication

Preparation of Material A4 for Solid Freeform Fabrication

Powder material A4 for solid freeform fabrication was prepared in the same manner as in the preparation of the powder material A1 for solid freeform fabrication except that polymethyl methacrylate (PMMA) was changed to polyester (PES, manufactured by Toray Industries, Inc.).

Preparation Example 5 of Material A for Solid Freeform Fabrication

Preparation of Material A5 for Solid Freeform Fabrication

Powder material A5 for solid freeform fabrication was prepared in the same manner as in the preparation of the powder material A1 for solid freeform fabrication except that polymethyl methacrylate (PMMA) was changed to polyether ether ketone (PEEK, manufactured by Victrex plc).

Preparation Example 6 of Material A for Solid Freeform Fabrication

Preparation of Material A6 for Solid Freeform Fabrication

Powder material A6 for solid freeform fabrication was prepared in the same manner as in the preparation of the powder material A1 for solid freeform fabrication except that polymethyl methacrylate (PMMA) was changed to zirconia (3YZ-E, manufactured by TOSOH CORPORATION).

Preparation Example 7 of Material A for Solid Freeform Fabrication

Preparation of Material A7 for Solid Freeform Fabrication

Powder material A7 for solid freeform fabrication was prepared in the same manner as in the preparation of the powder material A 1 for solid freeform fabrication except that polymethyl methacrylate (PMMA) was changed to alumina (AHP200, manufactured by Nippon Light Metal Company, Ltd.)

Preparation Example 8 of Material A for Solid Freeform Fabrication

Preparation of Material A8 for Solid Freeform Fabrication

Powder material A8 for solid freeform fabrication was prepared in the same manner as in the preparation of the powder material A1 for solid freeform fabrication except that polymethyl methacrylate (PMMA) was changed to silica (H201, manufactured by ASAHI GLASS CO., LTD.)

Preparation Example 9 of Material A for Solid Freeform Fabrication

Preparation of Material A9 for Solid Freeform Fabrication

Powder material A9 for forming a 3D object was prepared in the same manner as in the preparation of the powder material A1 for solid freeform fabrication except that polymethyl methacrylate (PMMA) was changed to lithium disilicate (prototype).

Preparation Example 10 of Material A for Solid Freeform Fabrication

Preparation of Material A10 for Solid Freeform Fabrication

Powder material 10 for fowling a 3D object was prepared in the same manner as in the preparation of the powder material A1 for solid freeform fabrication except that 1 part by mass of benzoyl peroxide (BPO) was changed to 5 parts of benzoyl peroxide (BPO).

Preparation Example 11 of Material A for Solid Freeform Fabrication

Preparation of Material A11 for Solid Freeform Fabrication

Powder material A11 for solid freeform fabrication was prepared in the same manner as in the preparation of the powder material A1 for solid freeform fabrication except that no benzoyl peroxide (BPO) was contained.

Preparation Example 12 of Material A for Solid Freeform Fabrication

Preparation of Material A12 for Solid Freeform Fabrication 40 parts by mass of polymethyl methacrylate (PMMA, manufactured by KURARAY CO., LTD.), 5 parts of benzoyl peroxide (BPO, manufactured by Tokyo Chemical Industry Co. Ltd.), 25 parts of methsyl methacrylate (MMA, manufactured by Tokyo Chemical Industry Co. Ltd.), and 30 parts of bisphenol A diglycidyl methacrylate (Bus-GMA, manufactured by Sigma-Aldrich Japan K.K.) were mixed to prepare a liquid material A12 for solid freeform fabrication. The solution had a viscosity of 113 mPa·s.

Preparation Example 13 of Material A for Solid Freeform Fabrication

Preparation of Material A13 for Solid Freeform Fabrication

Liquid material A13 for solid freeform fabrication was prepared in the same manner as in the preparation of the liquid material A12 for solid freeform fabrication except that polymethyl methacrylate was changed to polycarbonate (PC, manufactured by Mitsubishi Engineering-Plastics Corporation). The solution had a viscosity of 109 mPa·s.

Preparation Example 14 of Material A for Solid Freeform Fabrication

Preparation of Material A14 for Solid Freeform Fabrication

Liquid material A13 for solid freeform fabrication was prepared in the same manner as in the preparation of the liquid material A12 for solid freeform fabrication except that polymethyl methacrylate (PMMA) was changed to zirconia (3YZ-E, manufactured by TOSOH CORPORATION). The solution had a viscosity of 112 mPa·s.

Compositions and contents of the prepared materials A1-A14 for solid freeform fabrication were shown in Table 1.

TABLE 1

| No. of Material A for solid freeform fabrication | Organic particle or inorganic particle | | Polymerization compound A | | Polymerization initiator A Peroxide | | | Volume average particle diameter (μm) of organic particle and inorganic particle | Viscosity (25 degrees C.) (mPa·s) |
|---|---|---|---|---|---|---|---|---|---|
| | Kind | Material | Kind | Content (parts by mass) | Kind | Content (parts by mass) | State | | |
| 1 | Organic particle | PMMA | 100 | — | — | BPO | 1 | Powder | 40 | — |
| 2 | Organic particle | PC | 100 | — | — | BPO | 1 | Powder | 46 | — |
| 3 | Organic particle | PA12 | 100 | — | — | BPO | 1 | Powder | 62 | — |
| 4 | Organic particle | PES | 100 | — | — | BPO | 1 | Powder | 38 | — |
| 5 | Organic particle | PEEK | 100 | — | — | BPO | 1 | Powder | 55 | — |
| 6 | Inorganic particle | Zirconia | 100 | — | — | BPO | 1 | Powder | 42 | — |
| 7 | Inorganic particle | Alumina | 100 | — | — | BPO | 1 | Powder | 46 | — |
| 8 | Inorganic particle | Silica | 100 | — | — | BPO | 1 | Powder | 39 | — |
| 9 | Inorganic particle | Lithium disilicate | 100 | — | — | BPO | 1 | Powder | 53 | — |
| 10 | Organic particle | PMMA | 100 | — | — | BPO | 5 | Powder | 40 | — |
| 11 | Organic particle | PMMA | 100 | — | — | — | — | Powder | 40 | — |
| 12 | Organic particle | PMMA | 40 | MMA Bis-GMA | 25 30 | BPO | 5 | Liquid | 0.9 | 113 |
| 13 | Organic particle | PC | 40 | MMA Bis-GMA | 25 30 | BPO | 5 | Liquid | 0.8 | 109 |
| 14 | Inorganic particle | Zirconia | 40 | MMA Bis-GMA | 25 30 | BPO | 5 | Liquid | 0.3 | 112 |

Preparation Example 1 of Material B for Solid Freeform Fabrication

Preparation of Material B1 for Solid Freeform Fabrication 60 parts of methylmethacrylate (MMA, manufactured by Tokyo Chemical Industry Co. Ltd.) and 20 parts of 2-hydroxyethyl methacrylate (HEMA, manufactured by Tokyo Chemical Industry Co. Ltd.) as the mono-functional polymerizable compounds, 20 parts of bisphenol A diglycidyl methacrylate (Bis-GMA, manufactured by Sigma-Aldrich Japan K.K.) as the poly-functional polymerizable compound, and 1.5 parts of N,N-dimethyl-p-toluidine (DMPT, manufactured by Tokyo Chemical Industry Co. Ltd.) as tertiary amine were mixed to prepare a material B1 for solid freeform fabrication.

Preparation Example 2 of Material B for Solid Freeform Fabrication

Preparation of Material B2 for Solid Freeform Fabrication

Material B2 for solid freeform fabrication was prepared in the same manner as in the preparation of the material B1 for solid freeform fabrication except that 2-hydroxyethyl methacrylate (HEMA) was changed to hydroxy propyl methacrylate (HPMA, manufactured by Tokyo Chemical Industry Co. Ltd.).

Preparation Example 3 of Material B for Solid Freeform Fabrication

Preparation of Material B3 for Solid Freeform Fabrication

Material B3 for solid freeform fabrication was prepared in the same manner as in the preparation of the material B1 for solid freeform fabrication except that 2-hydroxyethyl methacrylate (HEMA) was changed to hydroxy butyl methacrylate (HBMA, manufactured by Kyoeisha Chemical Co., Ltd.).

Preparation Example 4 of Material B for Solid Freeform Fabrication

Preparation of Material B4 for Solid Freeform Fabrication

Material B4 for solid freeform fabrication was prepared in the same manner as in the preparation of the material B1 for solid freeform fabrication except that 20 parts by mass of 2-hydroxyethyl methacrylate (HEMA) was changed to 10 parts by mass of 2-hydroxyethyl methacrylate (HEMA).

Preparation Example 5 of Material B for Solid Freeform Fabrication

Preparation of Material B5 for Solid Freeform Fabrication

Material B5 for solid freeform fabrication was prepared in the same manner as in the preparation of the material B1 for solid freeform fabrication except that 20 parts by mass of 2-hydroxyethyl methacrylate (HEMA) was changed to 30 parts by mass of 2-hydroxyethyl methacrylate (HEMA).

Preparation Example 6 of Material B for Solid Freeform Fabrication

Preparation of Material B6 for Solid Freeform Fabrication

Material B6 for solid freeform fabrication was prepared in the same manner as in the preparation of the material B1 for solid freeform fabrication except that bisphenol A diglycidyl methacrylate (Bis-GMA) was changed to tetraethylene glycol dimethacrylate (TEGDMA, manufactured by Kyoeisha Chemical Co., Ltd.).

Preparation Example 7 of Material B for Solid Freeform Fabrication

Preparation of Material B7 for Solid Freeform Fabrication

Material B7 for solid freeform fabrication was prepared in the same manner as in the preparation of the material B1 for solid freeform fabrication except that bisphenol A diglycidyl methacrylate (Bis-GMA) was changed to urethane dimethacrylate (UDMA, manufactured by Sigma-Aldrich Japan K.K.).

Preparation Example 8 of Material B for Solid Freeform Fabrication

Preparation of Material B8 for Solid Freeform Fabrication

Material B8 for solid freeform fabrication was prepared in the same manner as in the preparation of the material B1 for solid freeform fabrication except that 20 parts of bisphenol A diglycidyl methacrylate (Bis-GMA) was changed to 10 parts of bisphenol A diglycidyl methacrylate (Bis-GMA).

Preparation Example 9 of Material B for Solid Freeform Fabrication

Preparation of Material B9 for Solid Freeform Fabrication

Material 9 for solid freeform fabrication was prepared in the same manner as in the preparation of the material B1 for solid freeform fabrication except that 20 parts of bisphenol A diglycidyl methacrylate (Bis-GMA) was changed to 30 parts of bisphenol A diglycidyl methacrylate (Bis-GMA).

Preparation Example 10 of Material B for Solid Freeform Fabrication

Preparation of Material B10 for Solid Freeform Fabrication

Material 10 for solid freeform fabrication was prepared in the same manner as in the preparation of the material B1 for solid freeform fabrication except that N,N-dimethyl-p-toluidine (DMPT) was changed to N,N-diethyl-p-toluidine (DEPT, manufactured by Tokyo Chemical Industry Co. Ltd.).

Preparation Example 11 of Material B for Solid Freeform Fabrication

Preparation of Material B11 for Solid Freeform Fabrication

Material B11 for solid freeform fabrication was prepared in the same manner as in the preparation of the material B1 for solid freeform fabrication except that 1.5 parts of N,N-dimethyl-p-toluidine (DMPT) was changed to 1 part of N,N-dimethyl-p-toluidine (DMPT).

Preparation Example 12 of Material B for Solid Freeform Fabrication

Preparation of Material B12 for Solid Freeform Fabrication

Material B12 for solid freeform fabrication was prepared in the same manner as in the preparation of the material B1 for solid freeform fabrication except that 1.5 parts of N,N-dimethyl-p-toluidine (DMPT) was changed to 5 parts of N,N-dimethyl-p-toluidine (DMPT).

Preparation Example 13 of Material B for Solid Freeform Fabrication

Preparation of Material B13 for Solid Freeform Fabrication

Material B13 for solid freeform fabrication was prepared in the same manner as in the preparation of the material B1 for solid freeform fabrication except that 20 parts of 2-hydroxyethyl methacrylate (HEMA), 20 parts of bisphenol A diglycidyl methacrylate (Bis-GMA), and viscosity of 10 mPa·s were changed to 10 parts of 2-hydroxyethyl methacrylate (HEMA), 10 parts of tetraethylene glycol dimethacrylate (TEGDMA), and viscosity of 4 mPa·s.

Preparation Example 14 of Material B for Solid Freeform Fabrication

Preparation of Material B14 for Solid Freeform Fabrication

Material B14 for solid freeform fabrication was prepared in the same manner as in the preparation of Liquid material B1 for solid freeform fabrication except that 20 parts of 2-hydroxyethyl methacrylate (HEMA), 20 parts of bisphenol A diglycidyl methacrylate (Bis-GMA), and viscosity of 10 mPa·s were changed to 30 parts of hydroxybutyl methacrylate (HBMA), 30 parts of bisphenol A diglycidyl methacrylate (Bis-GMA), and viscosity of 20 mPa·s.

Preparation Example 15 of Material B for Solid Freeform Fabrication

Preparation of Material B15 for Solid Freeform Fabrication

Material B15 for solid freeform fabrication was prepared in the same manner as in the preparation of the material B14 for solid freeform fabrication except that N,N-dimethyl-p-toluidine (DMPT) was changed to N-methylethane amine (MEA).

Preparation Example 16 of Material B for Solid Freeform Fabrication

Preparation of Material B16 for Solid Freeform Fabrication

Material B16 for solid freeform fabrication was prepared in the same manner as in the preparation of the material B14 for solid freeform fabrication except that no hydroxybutyl methacrylate (HBMA) was contained.

Preparation Example 17 of Material B for Solid Freeform Fabrication

Preparation of Material B17 for Solid Freeform Fabrication

Material B17 for solid freeform fabrication was prepared in the same manner as in the preparation of the material B16 for solid freeform fabrication except that no bisphenol A diglycidyl methacrylate (Bis-GMA) was contained.

Preparation Example 18 of Material B for Solid Freeform Fabrication

Preparation of Material B18 for Solid Freeform Fabrication

Material B18 for solid freeform fabrication was prepared in the same manner as in the preparation of the material B1 for solid freeform fabrication except that none of 60 parts of methylmethacrylate (MMA), 20 parts of 2-hydroxyethyl methacrylate (HEMA), or 20 parts of bisphenol A diglycidyl methacrylate (Bis-GMA)) was contained.

Compositions and contents of the prepared materials B1-B18 for solid freeform fabrication were shown in Table 2.

TABLE 2

| No. of Material B for solid freeform fabrication | Polymerizable compound B | | | | | | Polymerization initiator B | | Viscosity (25 degrees C.) (mPa · s) |
|---|---|---|---|---|---|---|---|---|---|
| | Mono-functional compound | | | | Poly-functional polymerizable compound | | Amine | | |
| | Kind 1 | Content of kind 1 (parts by mass) | Kind 2 | Number of carbon atoms in alkyl chain of HAMA | Content of kind 2 (parts by mass) | Kind | Content (parts by mass) | Kind | Content (parts by mass) | |
| 1 | MMA | 60 | HEMA | 2 | 20 | Bis-GMA | 20 | DMPT | 1.5 | 10 |
| 2 | MMA | 60 | HPMA | 3 | 20 | Bis-GMA | 20 | DMPT | 1.5 | 11 |
| 3 | MMA | 60 | HBMA | 4 | 20 | Bis-GMA | 20 | DMPT | 1.5 | 12 |
| 4 | MMA | 60 | HEMA | 2 | 10 | Bis-GMA | 20 | DMPT | 1.5 | 9 |
| 5 | MMA | 60 | HEMA | 2 | 30 | Bis-GMA | 20 | DMPT | 1.5 | 11 |
| 6 | MMA | 60 | HEMA | 2 | 20 | TEGDMA | 20 | DMPT | 1.5 | 7 |
| 7 | MMA | 60 | HEMA | 2 | 20 | UDMA | 20 | DMPT | 1.5 | 9 |
| 8 | MMA | 60 | HEMA | 2 | 20 | Bis-GMA | 10 | DMPT | 1.5 | 8 |
| 9 | MMA | 60 | HEMA | 2 | 20 | Bis-GMA | 30 | DMPT | 1.5 | 14 |
| 10 | MMA | 60 | HEMA | 2 | 20 | Bis-GMA | 20 | DEPT | 1.5 | 10 |
| 11 | MMA | 60 | HEMA | 2 | 20 | Bis-GMA | 20 | DMPT | 1 | 10 |
| 12 | MMA | 60 | HEMA | 2 | 20 | Bis-GMA | 20 | DMPT | 5 | 10 |
| 13 | MMA | 60 | HEMA | 2 | 10 | TEGDMA | 10 | DMPT | 1.5 | 4 |
| 14 | MMA | 60 | HBMA | 4 | 30 | Bis-GMA | 30 | DMPT | 1.5 | 20 |
| 15 | MMA | 60 | HBMA | 4 | 30 | Bis-GMA | 30 | MEA | 1.5 | 20 |
| 16 | MMA | 60 | — | — | — | Bis-GMA | 30 | DMPT | 1.5 | 20 |
| 17 | MMA | 60 | — | — | — | — | — | DMPT | 1.5 | 20 |
| 18 | — | — | — | — | — | — | — | DMPT | 1.5 | 5 |

In Table 2, HAMA represents hydroxy alkylmethacrylate and the number of carbon atoms in the alkyl chain of HAMA represents the number of carbons in the alkyl chain in HEMA, HPMA, or HBMA.

Example 1

The thus-obtained material A1 for solid freeform fabrication and the material B1 for solid freeform fabrication were combined as the material set for solid freeform fabrication (material set for additive manufacturing) of Example 1. Solid freeform object 1 was manufactured in the following manner based on a shape print pattern having a size of 70 mm long×12 mm wide using the material set for solid freeform fabrication.

1. Using a device (jig for powder, manufactured by "Ni-gata Kabushiki Kaisha") for fabricating a solid freeform object illustrated in FIG. 1, the material A1 for solid freeform fabrication was conveyed from the storage tank on the supplying side to the storage tank on the fabrication side and a thin layer of the material A1 for solid freeform fabrication having an average thickness of 100 μm was formed on the substrate mentioned above.

2. Next, the material B1 for solid freeform fabrication was applied (discharged) from the nozzle of an inkjet printer (SG7100, manufactured by Ricoh Company Ltd.) to the surface of the thus-formed thin layer of the material A1 for solid freeform fabrication to cure the material A1 for solid freeform fabrication.

3. Next, the operations 1 and 2 were repeated to sequentially laminate the thin layers of the cured material A for solid freeform fabrication until the total average thickness was a predetermined value, i.e., 3 mm, in order to fabricate the solid freeform object 1. The thus-obtained solid freeform object 1 did not lose shape when extra powder of the material A for solid freeform fabrication was removed by air blow. The solid freeform object 1 had a high level of strength and excellent dimension accuracy.

Next, the thus-obtained solid freeform object 1 was evaluated with regard to bending strength, bending elastic modulus, Vickers hardness, curing speed, and dimension accuracy according to the following criteria. The results are shown in Table 3.

Bending Strength and Bending Elastic Modulus

The bending strength of the thus-obtained solid freeform object 1 was measured by the three-point bending test according to JIS-T-6501 using a desktop precision universal testing machine (AUTOGRAPH-AGS-J, manufactured by Shimadzu Corporation) and the bending strength and the bending elastic modulus were evaluated according to the following evaluation criteria.

Evaluation Criteria of Bending Strength
G (Good): Not less than 80 MPa
M (Marginal): 50 MPa-less than 80 MPa
P (Poor) : Less than 50 MPa
Evaluation Criteria of Bending Elastic Modulus
G (Good): Not less than 2.0 GPa
M (Marginal): 1.5 GPa to less than 2.0 GPa
P (Poor): Less than 1.5 GPa Vickers Hardness Vickers hardness of the thus-obtained solid freeform object 1 was measured according to JIS-T-6501 using a Vickers hardness tester (FV-800, manufactured by FUTURE-TECH CORP) at a testing force of 0.2 kg and evaluated according to the following evaluation criteria.

Evaluation Criteria
G (Good): 18 HV0.2 or greater
M (Marginal): 10 HV0.2 to less than 18 HV0.2
P (Poor): Less than 10 HV0.2

Curing Speed

Curing speed of the solid freeform object 1 was evaluated according to the following criteria.

Evaluation Criteria
G (Good): State in which the obtained solid freeform object can be taken out by hands even only 10 seconds after the solid freeform fabrication
M (Marginal): State in which the obtained solid freeform object can be finally taken out by hands 10 minutes after the solid freeform fabrication
P (Poor): State in which the obtained solid freeform object is too brittle to be taken out even one hour after the solid freeform fabrication Dimension Accuracy Dimension accuracy of the solid freeform object 1 was evaluated according to the following criteria.

Evaluation Criteria
G (Good): The obtained solid freeform object has a smooth and aesthetic surface with no warp
M (Marginal): Surface of the obtained solid freeform object has slight distortion and slight warpage
P (Poor): Surface of the obtained solid freeform object has distortion and significant warpage Examples 2 to 26 and Comparative Examples 1 to 2

Preparation of Material Set for Solid Freeform Fabrication

Each solid freeform object (object produced by additive manufacturing) of Examples 2 to 26 and Comparative Examples 1 to 2 fabricated and evaluated in the same manner as in Example 1 except that the combination of the material A for solid freeform fabrication and the material B for solid freeform fabrication was changed as shown in Table 3. The results are shown in Table 3. Fabrication was not possible in Comparative Examples 1 and 2.

Example 27

The thus-obtained material A12 for solid freeform fabrication and the material B1 for solid freeform fabrication were combined as the material set for solid freeform fabrication (material set for additive manufacturing) of Example 27.

A solid freeform object (object produced by additive manufacturing) was fabricated and evaluated in the same manner as in Example 1 except that the fabrication process 1 was changed to the following 1'. The results are shown in Table 3.

1'. Using a device for fabricating a solid freeform object illustrated in FIG. 2, the material A12 for solid freeform fabrication was dropped from the storage tank on the supplying side to the storage tank on the fabrication side and a thin layer of the material A12 for solid freeform fabrication having an average thickness of 100 μm was formed on the substrate mentioned above.

Examples 28 to 29

Each solid freeform object (object produced by additive manufacturing) of Examples 28 to 29 was fabricated and evaluated in the same manner as in Example 27 except that the combination of the material A for solid freeform fabrication and the material B for solid freeform fabrication was changed as shown in Table 3. The results are shown in Table 3.

TABLE 3

|  |  | No. of material A for solid freeform fabrication | No. of material B for solid freeform fabrication | Amount of remaining monomer in solid freeform object | Bending strength (MPa) | Bending elastic modulus (GPa) | Vickers hardness (HV0.2) | Curing speed | Dimension accuracy |
|---|---|---|---|---|---|---|---|---|---|
| Example | 1 | 1 | 1 | 0.6 | G (105) | G (3.7) | G (23) | G | G |
|  | 2 | 2 | 1 | 0.8 | G (81) | G (2.5) | G (21) | G | G |
|  | 3 | 3 | 1 | 0.8 | G (83) | G (2.1) | G (22) | G | G |
|  | 4 | 4 | 1 | 0.6 | G (82) | G (2.3) | G (21) | G | G |
|  | 5 | 5 | 1 | 0.7 | G (86) | G (2.2) | G (21) | G | G |
|  | 6 | 6 | 1 | 0.9 | G (80) | G (2.3) | G (22) | G | G |
|  | 7 | 7 | 1 | 0.5 | G (81) | G (2.4) | G (21) | G | G |
|  | 8 | 8 | 1 | 1.0 | G (80) | G (2.2) | G (22) | G | G |
|  | 9 | 9 | 1 | 0.9 | G (83) | G (2.2) | G (21) | G | G |
|  | 10 | 1 | 2 | 0.8 | G (103) | G (3.8) | G (23) | G | G |
|  | 11 | 1 | 3 | 1.1 | G (92) | G (3.8) | G (24) | G | G |
|  | 12 | 1 | 4 | 1.0 | G (104) | G (3.7) | G (21) | G | G |
|  | 13 | 1 | 5 | 0.9 | G (98) | G (3.9) | G (22) | G | G |
|  | 14 | 1 | 6 | 1.8 | G (99) | G (3.2) | G (21) | M | G |
|  | 15 | 1 | 7 | 2.0 | G (106) | G (3.6) | G (25) | M | G |
|  | 16 | 1 | 8 | 1.7 | G (100) | G (3.2) | G (21) | M | G |
|  | 17 | 1 | 9 | 1.1 | G (107) | G (4.0) | G (25) | G | G |
|  | 18 | 1 | 10 | 1.2 | G (104) | G (3.7) | G (21) | G | G |
|  | 19 | 1 | 11 | 2.1 | G (104) | G (3.7) | G (21) | M | G |
|  | 20 | 1 | 12 | 0.9 | G (106) | G (3.6) | G (22) | G | G |
|  | 21 | 10 | 1 | 1.1 | G (122) | G (5.1) | G (28) | G | M |
|  | 22 | 1 | 13 | 0.6 | G (104) | G (3.6) | G (21) | G | M |
|  | 23 | 1 | 14 | 0.9 | G (105) | G (3.5) | G (22) | G | M |
|  | 24 | 1 | 15 | 2.2 | M (62) | M (1.6) | G (18) | M | M |
|  | 25 | 1 | 16 | 0.7 | G (92) | G (2.1) | G (21) | G | G |
|  | 26 | 1 | 17 | 0.6 | M (54) | M (1.5) | M (14) | G | G |
|  | 27 | 12 | 1 | 0.6 | G (134) | G (4.0) | G (22) | G | G |
|  | 28 | 13 | 1 | 0.5 | G (128) | G (3.9) | G (24) | G | G |
|  | 29 | 14 | 1 | 0.6 | G (221) | G (4.5) | G (28) | G | G |
| Comparative Example | 1 | 11 | 1 | 92.6 | Unable to fabricate | | | | |
|  | 2 | 1 | 18 | 0.0 | Unable to fabricate | | | | |

In Table 3, the values of bending strength, bending elastic modulus, and Vickers hardness were shown in parentheses situated on the side of the evaluation.

Embodiments of the present disclosure are, for example, as follows.

1. A solid freeform fabrication material set includes a material A for solid freeform fabrication including a polymerization initiator A and at least one of an organic particle and an inorganic particle and a material B for solid freeform fabrication including a polymerizable compound B.

2. The solid freeform fabrication material set according to 1 mentioned above, wherein the organic particle includes at least one of polymethyl methacrylate, polycarbonate, polyester, polyamide, and polyether ether ketone.

3. The solid freeform fabrication material set according to 1 or 2 mentioned above, wherein the inorganic particle includes at least one of zirconia, alumina, and silicate.

4. The solid freeform fabrication material set according to any one of 1 to 3 mentioned above, wherein the polymerization initiator A includes a peroxide.

5. The solid freeform fabrication material set according to any one of 1 to 4 mentioned above, wherein when the material A for solid freeform fabrication is liquid, the volume average particle diameter of at least one of the organic particle and the inorganic particle is less than 1 μm, and wherein the material A for solid freeform fabrication is powder, the volume average particle diameter of at least one of the organic particle and the inorganic particle is not less than 1 μm.

6. The solid freeform fabrication material set according to any eon of 1 to 5 mentioned above, wherein the material A for solid freeform fabrication further includes a polymerizable compound A.

7. The solid freeform fabrication material set according to any one of 1 to 6 mentioned above, wherein both the material A for solid freeform fabrication and the material B for solid freeform fabrication are liquid.

8. The solid freeform fabrication material set according to any one of 1 to 6 mentioned above, wherein the material A for solid freeform fabrication is powder and the material B for solid freeform fabrication is liquid.

9. The solid freeform fabrication material set according to any one of 1 to 8 mentioned above, wherein the material B for solid freeform fabrication further includes a tertiary amine as a polymerization initiator.

10. The solid freeform fabrication material set according to any one of 6 to 9 mentioned above, wherein the polymerizable compound A or the polymerizable compound B includes a mono-functional polymerizable compound and a polyfunctional polymerizable compound.

11. The solid freeform fabrication material set according to 10 mentioned above, wherein the mono-functional polymerizable compound or the polyfunctional polymerizable compound includes at least one of an acrylic compound and a methacrylic compound.

12. The solid freeform fabrication material set according to any one of 9 to 11 mentioned above, wherein the tertiary amine has a toluidine backbone.

13. A method of fabricating a solid freeform object includes forming a layer of the material A for solid freeform fabrication using the material A for solid freeform fabrication in the solid freeform fabrication material set according to any one of 1 to 12 mentioned above, applying the material B for solid freeform fabrication in the solid freeform fabrication material set for solid freeform fabrication of any one of 1 to 12 mentioned above to a predetermined area of the layer of the material A for solid freeform fabrication, and repeating the forming and the applying.

14. A method of fabricating a dental prosthesis includes forming a layer of the material A for solid freeform fabrication using the material A for solid freeform fabrication in the solid freeform fabrication material set according to any one of 1 to 12 mentioned above, applying the material B for solid freeform fabrication in the solid freeform fabrication material set of any one of 1 to 12 mentioned above to a predetermined area of the layer of the material A for solid freeform fabrication, and repeating the forming and the applying.

15. A device for fabricating a solid freeform object includes a layer forming device to form a layer of the material A for solid freeform fabrication using the material A for solid freeform fabrication in the solid freeform fabrication material set of any one of 1 to 12 mentioned above and a liquid applying device to apply the material B for solid freeform fabrication in the solid freeform fabrication material set of any one of 1 to 12 mentioned above to a predetermined area of the layer of the material A for solid freeform fabrication.

The present disclosure provides a solid freeform fabrication material set by which complex three-dimensional objects can be easily and efficiently fabricated and the obtained object has good strength even immediately after fabrication.

Having now fully described embodiments of the present invention, it will be apparent to one of ordinary skill in the art that many changes and modifications can be made thereto without departing from the spirit and scope of embodiments of the invention as set forth herein.

What is claimed is:

1. A method of fabricating a solid freeform object, the method comprising:
   forming a layer of a material A comprising a polymerization initiator A, a polymerizable compound A, and at least one of an organic particle and an inorganic particle;
   applying a material B comprising a polymerizable compound B to a predetermined area of the layer of material A such that a layer of a cured product of the material A and the material B is obtained; and
   repeating the forming of the material A and the applying of the material B,
   wherein both the material A and the material B are liquid, and
   wherein a volume average particle diameter of the at least one of the organic particle and the inorganic particle of the material A is less than 1 µm.

2. A method according to claim 1, wherein the solid freeform object is a dental prosthesis.

3. A device for fabricating a solid freeform object, comprising:
   a layer forming device configured to form a layer of a material A comprising a polymerization initiator A, a polymerizable compound A, and at least one of an organic particle and an inorganic particle; and
   a liquid applying device configured to apply a material B comprising a polymerizable compound B to a predetermined area of the layer of material A such that a layer of a cured product of the material A and the material B is obtained,
   wherein both the material A and the material B are liquid, and
   wherein a volume average particle diameter of the at least one of the organic particle and the inorganic particle of the material A is less than 1 µm.

4. The method according to claim 1, wherein the organic particle comprises at least one selected from the group consisting of a polymethyl methacrylate, a polycarbonate, a polyester, a polyamide, and a polyether ether ketone.

5. The method according to claim 1, wherein the inorganic particle comprises at least one selected from the group consisting of zirconia, alumina, and a silicate.

6. The method according to claim 1, wherein the polymerization initiator A comprises a peroxide.

7. The method according to claim 1, wherein the material B further comprises a tertiary amine as a polymerization initiator B.

8. The method according to claim 1, wherein the polymerizable compound A or the polymerizable compound B comprises a mono-functional polymerizable compound and a polyfunctional polymerizable compound.

9. The method according to claim 8, wherein the mono-functional polymerizable compound or the polyfunctional polymerizable compound comprises at least one selected from the group consisting of an acrylic compound and a methacrylic compound.

10. The method according to claim 7, wherein the tertiary amine has a toluidine backbone.

11. The device according to claim 3, wherein the organic particle comprises at least one selected from the group consisting of a polymethyl methacrylate, a polycarbonate, a polyester, a polyamide, and a polyether ether ketone.

12. The device according to claim 3, the inorganic particle comprises at least one selected from the group consisting of zirconia, alumina, and a silicate.

13. The device according to claim 3, wherein the polymerization initiator A comprises a peroxide.

14. The device according to claim 3, wherein the material B further comprises a tertiary amine as a polymerization initiator B.

15. The device according to claim 3, wherein the polymerizable compound A or the polymerizable compound B comprises a mono-functional polymerizable compound and a polyfunctional polymerizable compound.

16. The device according to claim 15, wherein the mono-functional polymerizable compound or the polyfunctional polymerizable compound comprises at least one selected from the group consisting of an acrylic compound and a methacrylic compound.

17. The device according to claim 14, wherein the tertiary amine has a toluidine backbone.

* * * * *